United States Patent [19]

Guay

[11] 4,418,692

[45] Dec. 6, 1983

[54] DEVICE FOR TREATING LIVING TISSUE WITH AN ELECTRIC CURRENT

[76] Inventor: Jean-Louis Guay, 8770 Moorhead Cir., E., Boulder, Colo. 80303

[21] Appl. No.: 961,569

[22] Filed: Nov. 17, 1978

[51] Int. Cl.$^3$ .............................................. A61B 17/39
[52] U.S. Cl. ............................ 128/303.14; 128/303.17
[58] Field of Search ...................... 128/303.13–303.18, 128/800

[56] References Cited

U.S. PATENT DOCUMENTS

| | | | |
|---|---|---|---|
| 1,978,495 | 10/1934 | Landau | 128/303.16 |
| 3,920,021 | 11/1975 | Hiltebrandt | 128/303.17 |
| 4,016,881 | 4/1977 | Rioux et al. | 128/303.17 |
| 4,054,143 | 10/1977 | Bauer | 128/303.17 |

FOREIGN PATENT DOCUMENTS

| | | | |
|---|---|---|---|
| 2325626 | 11/1974 | Fed. Rep. of Germany | 128/303.17 |
| 2415263 | 10/1975 | Fed. Rep. of Germany | 123/303.17 |
| 2355521 | 1/1978 | France | 128/303.17 |

Primary Examiner—Lee S. Cohen

[57] ABSTRACT

A device is disclosed for use in a laparoscopic tubal cauterization for blocking the fallopian tubes of a patient. The device comprises a substantially tubular body member having a piston slidably mounted therein. A spring urges the piston to a first position relative to the body member. A button extends from one end of the body member for moving the piston to a second position against the urging of the spring. First and second electrodes are incorporated for either monopolar or bipolar treatment of the living tissue. The first and second electrodes are disposed to grasp the living tissue when the piston is in the first position and to release the living tissue when the piston is in the second position. The invention includes a circuit breaker for terminating continuity when the piston is disposed in the second position. An activating switch is disabled when the piston is in the second position. The invention provides a dual series switch system of circuit interruption when the electrodes release the living tissue.

19 Claims, 11 Drawing Figures

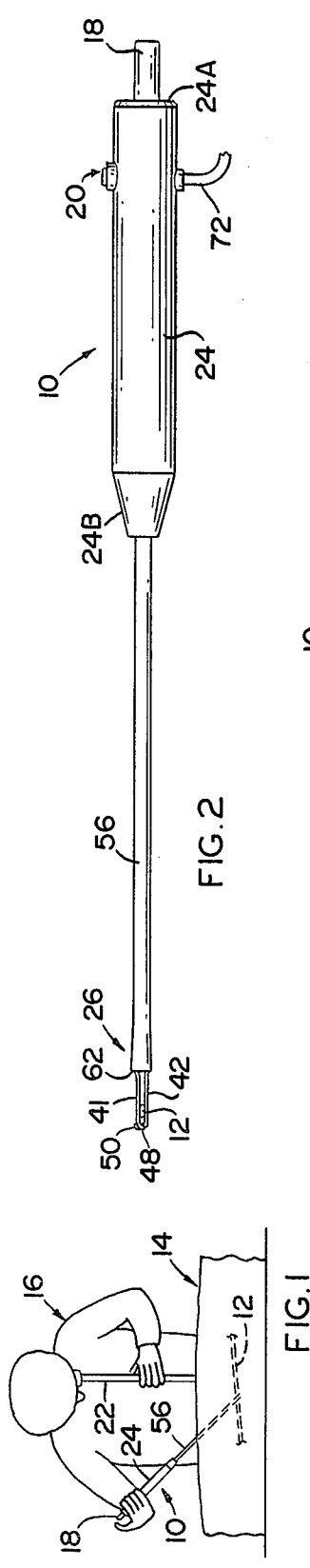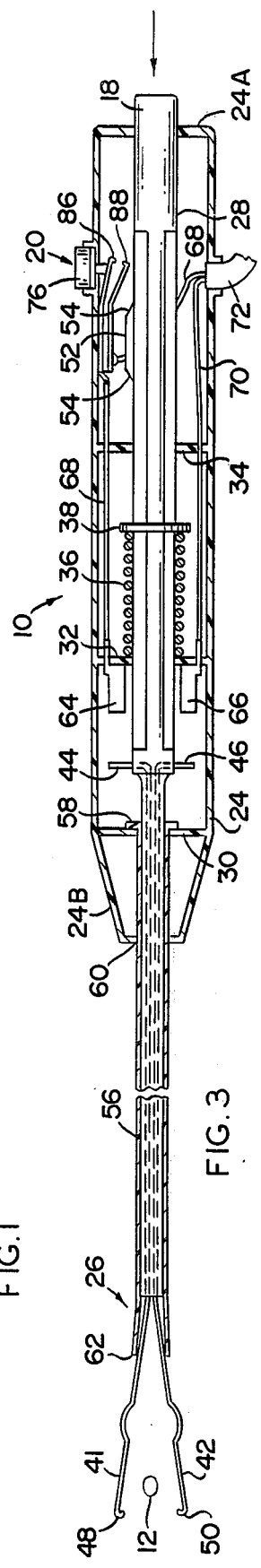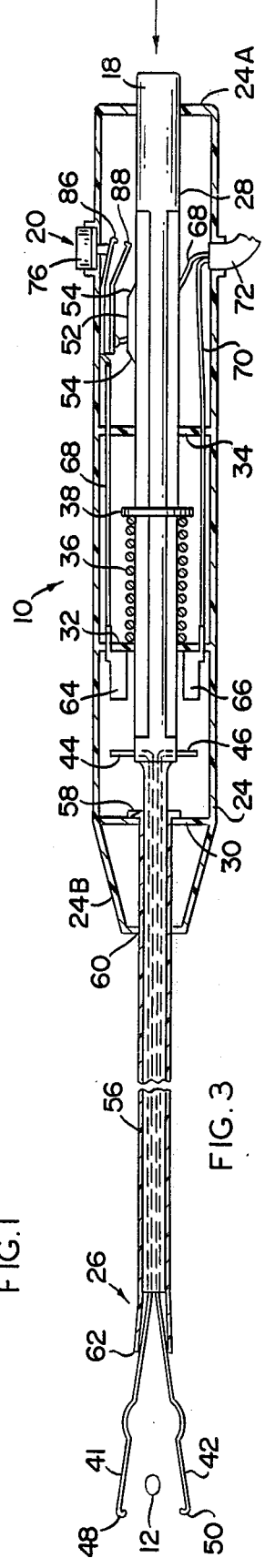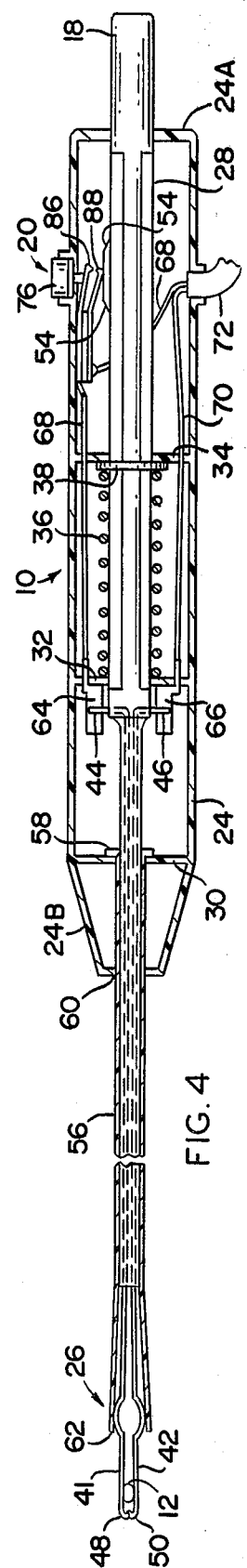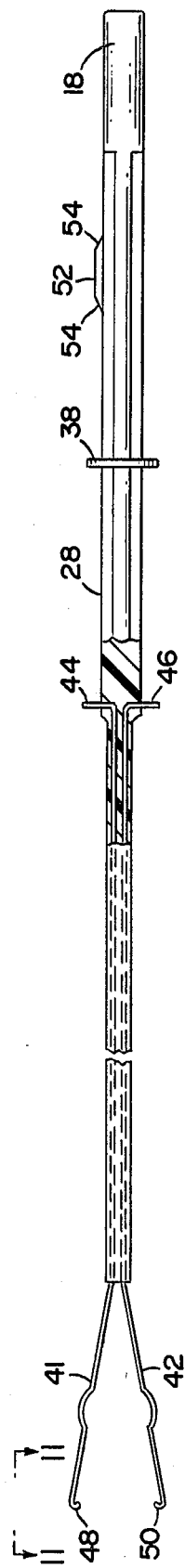

DEVICE FOR TREATING LIVING TISSUE WITH AN ELECTRIC CURRENT

FIELD OF THE INVENTION

This invention relates to medical instruments and more particularly to a device for treating living tissue with an electric current suitable for use in laparoscopic tubal cauterization.

BACKGROUND OF THE INVENTION

The procedure of female sterilization by laparoscopic tubular cauterization has provided the most efficient and least painful method of sterilization of women. Under this procedure, the fallopian tubes are cauterized with an electrical current from an electrical power source. Both monopolar and bipolar treatment have been used in the cauterization of fallopian tubes.

In the monopolar cauterization, the patient is physically placed upon a metallic base plate connected to one side of the electrical power source. An electrode which is connected to the other side of the power source is inserted into the abdomen of the patient through the use of a trocar or the like. Accordingly, the electric current passes between the inserted electrode and the metallic base plate through the living tissue. The monopolar device had the distinct disadvantage of controlling the flow of current between the inserted electrode and the base plate. In addition, the surgeon is required to take great care to insure that the device is not activated prior to proper positioning within the abdomen of the patient. Otherwise, the electrical current from the device will flow in an undesirable direction thereby damaging adjacent tissue.

This disadvantage of the monopolar device was overcome with the introduction of a bipolar device comprising a first and a second electrode insertable into the abdomen of the patient. In the bipolar device, the living tissue is grasped between the first and second electrode thereby controlling the electrical current through the living tissue between the first and second electrodes. Unfortunately, the design of the bipolar devices has not met the needs of the art. Primarily, the prior art devices are difficult to control by the surgeon and required the surgeon to physically grasp the living tissue by the use of a trigger, lever or the like against the urging of a spring. Simultaneously therewith, a switch had to be depressed to pass electrical current between the first and second electrodes. These two movements make the prior art devices awkward to use by a surgeon.

The prior art bipolar devices do not provide for a safety interlock to prevent the accidental activation of the device prior to proper positioning within the abdomen of the patient. Still a further disadvantage of the prior art devices was the inability of the bipolar units to cut the living tissue. In general, the cutting of living tissue requires a small area electrode adjacent a large area electrode thereby intensifying the electric field to provide sufficient current to cut the living tissue upon an increased current flow thereto. In the prior art bipolar devices, the first and second electrodes are substantially identical and do not permit the cutting of tissue. Many surgeons prefer to cut the fallopian tubes after cauterization rather than to merely rely on the blockage caused by the cauterization. In such instances, one device is needed for cauterizing and one device is needed to sever the fallopian tubes.

Therefore it is an object of this invention to provide an apparatus which overcomes the aforementioned inadequacies of the prior art devices and provides an improvement which is a significant contribution to the advancement of the sterilization art.

Another object of this invention is to provide a device for treating living tissue with an electrical current from an electrical power source wherein the device may be used either as a bipolar or a monopolar device and capable of either cauterizing or severing living tissue.

Another object of this invention is to provide a device for treating living tissue with an electrical current from an electrical power source comprising a piston slidably mounted in a body with urging means urging the piston to a first position with a first and a second electrode disposed to grasp the living tissue when the piston is urged to the first position. The urging means of the device will continually grasp the living tissue disposed between the first and the second electrode elements.

Another object of this invention is to provide a device for treating living tissue with an electrical current from an electrical power source comprising circuit breaker means for terminating continuity to the electrodes when the piston is in the second position thereby making the device incapable of operation until the electrodes are grasping the tissue.

Another object of this invention is to provide a device for treating living tissue with an electrical current from an electrical power source including a switch for activating electrical power to the electrodes with means for disabling the switch when the piston is in the second position.

Another object of this invention is to provide a device for treating living tissue with an electrical current from an electrical power source wherein the device may be easily manufactured as a disposable single use item.

The foregoing has outlined some of the more pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description describing the preferred embodiment, in addition to the scope of the invention defined by the claims taken in conjunction with the accompanying drawings.

SUMMARY OF THE INVENTION

The invention is defined by the appended claims to cover the disclosed embodiments shown in the attached drawings and the equivalent thereof as set forth in the detailed discussion. For the purpose of summarizing the invention, the invention may be incorporated into a device for treating living tissue with an electric current from an electrical power source. The device comprises a body member and a piston slidably mounted relative to the body member. Urging means, such as a spring, urges the piston to a first position relative to the body member. Means are provided for moving the piston to a second position relative to the body member against the urging means. A first and a second electrode element is mounted with the first electrode element moving in accordance with the movement of the piston. The first and second electrode elements are disposed to grasp the living tissue when the piston is in the first position whereas the electrodes release the living tissue when the piston is in the second position. The first and second electrodes are connected to the electrical power source to provide an electrical current flow relative to the living tissue.

In a more specific example of the invention, a circuit breaker is included for terminating continuity to the electrode elements when the piston is in the second position. This eliminates the possibility of accidental triggering of the device or static electricity discharge accumulated in the electrodes and wires of the device when the first and second electrodes are in the open position. The first and second electrodes may be moved into the open position by a button extending from a first end of the body member for moving the piston to the second position. In this embodiment, the first and the second electrodes extend from the second end of the body member such that the piston slidably extends along the axis of a substantially cylindrical body member. A switch is disposed on one surface of the body member for connecting the electrical power source to the electrode elements. Means such as a projection on the piston is provided for disabling the switch when the piston is in the second position. This configuration provides a second safety interlock for preventing accidental electrification of the electrodes when the first and second electrode elements are in the open position. The switch means is connected in electrical series with the circuit breakers thereby providing a series switch interconnection system.

Various configurations of the electrode elements may be devised for the device. In one embodiment, the first electrode element moves relative to the second electrode element upon movement of the piston. The movement of the first and second electrodes are in a diverse direction upon longitudinal movement of the piston. The first and second electrode elements may both be mounted on the piston. In another embodiment, only the first electrode element is mounted to the piston and the second electrode element is secured to the body member. The piston may be integrally molded to contain a first electrode element with the piston slidably received in a sleeve extending from the second end of the body. The first element is biased to diverge relative to the second electrode element upon a longitudinal movement of the piston toward the second position. Each of the first and second electrodes may be secured to the piston with an inwardly projecting tab extending from the terminal end thereof. The electrodes open upon movement of the piston to the second position and grasp the living tissue by releasing of the button.

In another embodiment, the second electrode is secured to the body member in fixed spatial relationship. The first electrode element diverges relative to the second electrode element upon longitudinal movement of the piston relative to the body member.

In still a further embodiment, the first electrode element terminates in a hook whereas the second electrode element terminates in a projection. The hook has a greater electrode area than the projection for cutting tissue between the first and second electrode elements.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 is an elevational view of a surgeon utilizing the new improved device in a laparoscopic cauterization process;

FIG. 2 is a magnified elevational view of the device shown in FIG. 1;

FIG. 3 is a sectional view of the device shown in FIG. 2 illustrating the piston in a second position;

FIG. 4 is a sectional view of the device shown in FIG. 2 illustrating the piston in a first position;

FIG. 5 is an enlarged view of the piston shown in the devices in FIGS. 1-4;

Figure 6:
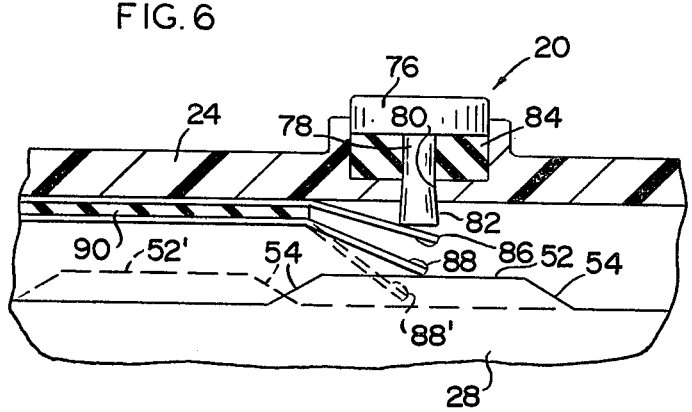
FIG. 6 is a magnified view of the switch assembly shown in FIGS. 3 and 4.

Similar reference characters refer to similar parts through the several views of the drawings. For a more clearer understanding of the invention, the following number identifications taken in connection with the detailed description and the drawings set forth the preferred mode or practice of the invention.

| 10 | device | 64 | contact pad |
|----|--------|----|-------------|
| 12 | tissue | 66 | contact pad |
| 14 | patient | 68 | wire |
| 16 | physician | 70 | wire |
| 18 | button | 72 | cable |
| 20 | activation switch | 76 | actuator |
| 22 | abdominal optical device | 78 | stem |
| 24 | body member | 80 | aperture |
| 24A | first end | 82 | enlarged region |
| 24B | second end | 84 | resilient material |
| 26 | electrode | 86 | first contact element |
| 28 | piston | 88 | second contact element |
| 30 | guide | 88' | phantom position |
| 32 | guide | 90 | insulator |
| 34 | guide | 128 | piston |
| 36 | spring | 141 | first electrode |
| 38 | flange | 142 | second electrode |
| 41 | first electrode | 144 | contact arm |
| 42 | second electrode | 146 | contact arm |
| 44 | contact arm | 156 | sleeve |
| 46 | contact arm | 164 | contact pad |

| | | | |
|---|---|---|---|
| 48 | inwardly projecting tab | 166 | contact pad |
| 50 | inwardly projecting tab | 228 | piston |
| 52 | elevated region | 241 | first electrode |
| 52' | phantom position | 242 | second electrode |
| 54 | ramp | 244 | contact arm |
| 56 | sleeve | 246 | contact arm |
| 58 | flange | 264 | contact pad |
| 60 | aperture | 266 | contact pad |
| 62 | terminal end | | |

DETAILED DESCRIPTION

FIGS. 1-6 illustrate a device 10 for treating living tissue 12, such as the blocking of a fallopian tube 12 of a patient 14 by laparoscopic tubal cauterization. The device 10 is specifically designed to enable a physician 16 to conveniently hold the device 10 and grasp the tissue 12 by the manipulation of a button 18 conveniently located at a terminal end of the device 10. The specific position of the button 18 and an activation switch 20 permits the physician 16 to easily manipulate the device 10 while viewing the fallopian tube 12 through an abdominal optical device 22. The device 10 is primarily designed to be a disposable device which is convenient to operate and inexpensive to manufacture. Although the device 10 is disclosed with reference to the laparoscopic tubal cauterization for blocking fallopian tubes of a patient, it should be understood that the principles and invention set forth herein are applicable to other electrical surgical treatments and the application disclosed herein should not be construed as a limitation on the claimed subject matter.

Figure 11:
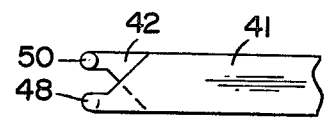
FIG. 11 is a view along line 11—11 in FIG. 5.

FIG. 2 illustrates an enlarged view of the device 10 with FIGS. 3 and 4 being sectional views of the device of FIG. 2. FIG. 3 illustrates the electrode elements of the device 10 in an open position whereas FIG. 4 illustrates the electrode elements in a closed position and grasping the fallopian tube 12. The device 10 comprises a substantially cylindrical body member 24 with the button 18 extending from a first end 24A of the body member 24 and with the electrodes 26 extending from a second end 24B of the body member 24, into a sleeve 56 where they are slidably received and further extends from terminal end 62 of sleeve 56. A piston 28 shown enlarged in FIG. 5 is slidably received within the body member 24 by guides 30, 32 and 34. An urging means biases the piston 28 into a first position shown in FIG. 4 relative to body member 24 and sleeve 56. The urging means includes a spring 36 coacting between guide 32 and a flange 38 extending from piston 28 to urge the piston 28 into the first position shown in FIG. 4. Depressing button 18 causes the piston 28 to move into a second position, relative to body member 24 and sleeve 56 shown in FIG. 3, against the urging of spring 36. The piston 28 may be integrally molded to contain the electrode means 26. In this example, a first and a second electrode 41 and 42 extends along an internal region of piston 28 and terminate as contact arms 44 and 46 extending perpendicularly to the axis of piston 28. Each of the electrodes 41 and 42 has an inwardly projecting tab 48 and 50 for grasping the fallopian tube 12. FIG. 11 is an elevational view along line 11—11 showing in greater detail the specific configuration of the electrodes 41 and 42.

Piston 28 also comprises an elevated region 52 having a tapered ramp 54 interconnecting the elevated region 52 with the surface of the piston 28. The function of the elevated region 52 will be explained hereinafter. The piston 28 and the electrodes 41 and 42 are may be united in a single injection molding process. The formed electrodes 41 and 42 may be positioned within a mold cavity prior to introduction of a plastic material into the mold cavity.

A sleeve 56 has an outwardly projecting annular flange 58 which abuts guide 30 as the sleeve 56 extends through an aperture 60 in the second end 24B of the body member 24 to fixably mount sleeve 56. The piston 28 is slidably received within the sleeve 56 such that terminal end 62 of sleeve 56 controls the biased divergence and convergence of the first and second electrodes 41 and 42 upon a reciprocating longitudinal movement of piston 28. A first and a second contact pad 64 and 66 are secured to guide 32 and connected to wires 68 and 70 which extend through power cable 72 to an electrical power source (not shown). Wire 70 extends directly into cable 72 whereas wire 68, which is preferably connected to the ungrounded terminal of the electrical power source, extends through the switch 20 which is more fully shown in FIG. 6. Switch 20 comprises a switch activator 76 shown as a button having a stem 78 which extends through an aperture 80 in the body member 24. The stem 78 terminates in an enlarged region 82 which retains activator 76 to the body member 24 after the enlarged region 82 is initially forced through aperture 80 in the body member 24. A suitable resilient material 84 biases the activator 76 into the outward position as shown in FIG. 6. The switch 20 comprises a first and a second contact element 86 and 88 separated by an electrical insulator 90. The first and second contact elements 86 and 88 are interposed in wire 68 shown in FIGS. 3 and 4 to enable electrical continuity only upon physical contact of the first and second contact elements 86 and 88. The second contact element 88 is biased toward a phantom position 88' whereat depression of activator 76 will not cause physical contact between the first and second contact elements 86 and 88. When piston 28 is in the first position the elevated region 52 moves the second contact element 88 into the solid position shown in FIG. 6. Accordingly, depression of activator 76 will cause physical contact between first and second contact elements 86 and 88.

The operation of the device 10 may be explained with reference to FIGS. 1-6. The first and second electrodes 41 and 42 and sleeve 56 are inserted into the abdomen of the patient 14 through the use of a trocar or similar device. The physician 14 depresses button 18 into the second position shown in FIG. 3 while investigating the abdominal cavity. When piston 28 is in the second position, the contact arms 44 and 46 are displaced from contact pads 64 and 66. This circuit breaker reduces the possibility of accidental activation of the device 10 in addition to reducing static discharge from any charge stored in the capacitance of cable 72. Elevated region 52 is also moved into the phantom position 52' to disable switch 20. The combination of a circuit breaker in series with a disabled switch reduces the possibility of accidental discharge of the device 10 during the preliminary steps of identifying the proper tissue by the physician. The problem of accidental activation in the prior art has been a substantial area of concern for the treating physician. Inadvertent activation or capacitance discharge of the device 10 can cause severe damage to adjacent tissue which can result in substantial liability for the treating physician. The use of plural switching elements in electrical series substantially reduces this hazard.

The first and second electrodes 41 and 42 diverge upon a longitudinal movement of piston 28 to the second position in FIG. 3 to enable the fallopian tube 12 to be grasped by the physician 16. Upon identifying the fallopian tube 12, the physician releases button 18 enabling spring 36 to return piston 28 to the first position shown in FIG. 4. The first and second electrodes 41 and 42 and the inwardly projecting tabs 48 and 50 withdraws thus converging and grasping the fallopian tube 12. Contact arms 44 and 46 engage the contact pads 64 and 66 while the elevated region 52 moves the second contact element 88 into the solid position shown in FIG. 6. The treating physician merely depresses activator 76 to produce electrical current flow between the first and second electrodes 41 and 42 to seal the fallopian tubes 12.

It should be appreciated that the device 10 maintains the grasp on the tissue during the electrical current flow process. The prior art devices required the treating physician to actively maintain tension to hold the fallopian tubes while activating the device. The combination of these two hand movements made the prior art devices difficult to operate. The present invention eliminates the need of compound function by the treating physician. During the grasping process, only button 18 is manipulated by the physician. After grasping the tissue, only activator 76 is manipulated by the physician.

After treatment of the fallopian tube 12, button 18 is depressed to release the treated tissue from the electrodes 41 and 42. The device 10 may then be withdrawn from the abdomen of the patient 14. Depression of button 18 opens the electrical circuit at contact arms 44 and 46 and disables switch 20.

It should be appreciated that the device 10 shown in FIGS. 1–6 is constructed of only a few relatively simple components. The molded plastic piston 28 and electrodes 41 and 42 are slidably received in plastic body member 24. The sleeve 56 is held into position by flange 58 and aperture 60. The contact pads 64 and 66 are pressed into slots (not shown) in guide 32 with the switch 20 being preassembled for quick installation into the body member 24. The configuration set forth in FIGS. 1–6 provides a simple, reliable, safe and inexpensive disposable unit for the electrical treatment of living tissue.

Figure 7:
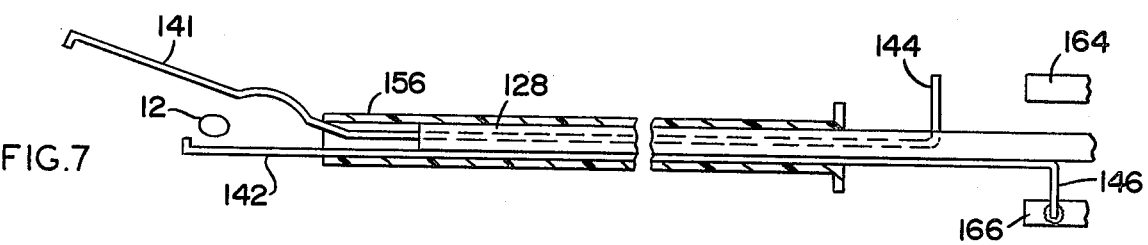
FIG. 7 is a first variation of a first and a second electrode when the piston is disposed in the second position.
Figure 8:
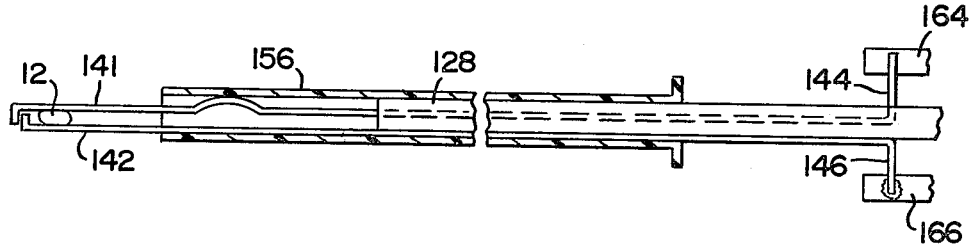
FIG. 8 is the first variation of a first and a second electrode shown in FIG. 7 when the piston is disposed in the first position.

FIGS. 7 and 8 illustrate a variation of the piston and electrode assembly in the second and first position respectively. This variation is suitable for use with the body member 24 of the device 10 shown in FIGS. 1–6. In this embodiment, a first electrode 141 is secured to piston 128 whereas a second electrode 142 is mounted to a body member (not shown). Contact arm 144 moves in relation to contact pad 164 upon movement of piston 128, whereas contact arm 146 is continuously connected to contact pad 166. The first electrode 141 is biased to diverge relative to the second electrode 142 upon a longitudinal movement of the piston 128. Sleeve 156 controls the divergence of the first electrode 141 relative to the second electrode 142. FIG. 8 illustrates the effect of the spring bias moving the piston 128 to the first position. The first electrode 141 converges relative to the second electrode 142 to grasp the tissue therebetween. Concomitently therewith, contact arm 144 engages contact pad 164.

The embodiment shown in FIGS. 7 and 8 provides a device where the second electrode 142 does not move relative to body member 24 upon movement of piston 28. In FIGS. 3 and 4, the electrodes 41 and 42 move relative to the body member 24 upon movement of piston 28. In FIGS. 3 and 4, the physician 16 must compensate for the movement of the electrodes 41 and 42 upon releasing button 18. In FIGS. 7 and 8, the physician 16 merely positions the fallopian tube 14 adjacent electrode 142 and releases button 18 to allow the first electrode 141 to grasp the fallopian tube 14.

Figure 9:
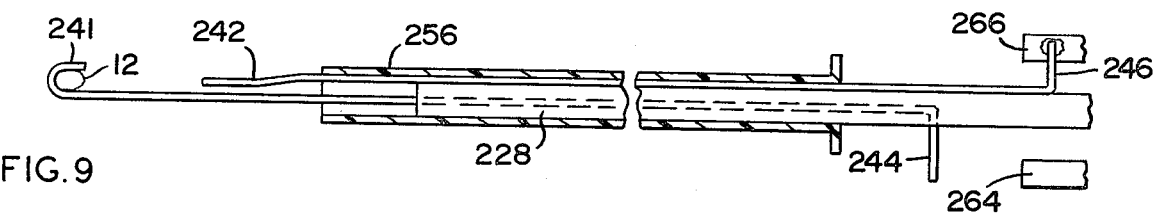
FIG. 9 is a second variation of a first and a second electrode when the piston is disposed in a second position.
Figure 10:
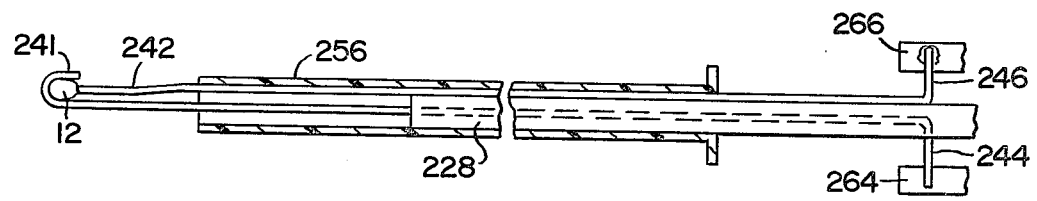
FIG. 10 is the second variation of the first and second electrode shown in FIG. 9 with the piston being disposed in the first position.

FIGS. 9 and 10 show a second variation of the piston electrode assembly in the second and first position respectively. In this embodiment, the first electrode 241 comprises a substantial hook-shaped electrode whereas the second electrode 242 is a projection. The hook 241 has a greater area than the projection 242 to cut tissue between the first and second electrode elements 241 and 242. In a similar manner as FIGS. 7 and 8, the second electrode 242 is fixed relative to the body member (not shown) with the contact arm 246 engaging contact pad 266. The first electrode 241 is secured to piston 228 to move longitudinally between the first and the second position. Contact arm 244 moves relative to contact pad 264 as heretofore described. In this example, the first and second electrodes 241 and 242 merely move longitudinally relative to one another rather than in compound longitudinal and divergent movement. The electrode configurations shown in FIGS. 9 and 10 have the advantage of enabling the fallopian tube 12 to be hooked by the first electrode 241 prior to enagagement with the second engagement 242. In addition, the difference in electrode area between the first and second electrodes 241 and 242 enables the tissue to be first cauterized by a first level of electrical current flow between the first and second electrodes and to be subsequently severed by an increase of electrical current flow therebetween. In the prior art, two devices and two insertions had to be utilized to first cauterize and secondly to sever the fallopian tube. With the present invention, both processes may be done by the same device during the same insertion by merely an increase in power level of the electrical current flow between the first and second electrodes 241 and 242.

The embodiment shown in FIGS. 1–11 illustrate various unique features of the invention. It should be understood that various aspects of each of the specific embodiments may be utilized and interchanged with other embodiments to obtain additional advantages and benefits which are within the ordinary scope of those skilled in the art. Further, various types of physical arrangements of parts and component structures may be modified and utilized for adapting the device for other applications and uses. These modifications are also considered to be within the scope of the invention and the appended claims.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of the circuit and the combination and arrangement of circuit elements may be resorted to without departing from the spirit and scope of the invention.

Now that the invention has been described:
What is claimed is:

1. A device for treating living tissue with an electrical current from a power source, comprising in combination:
   a substantially cylindrical body member having a first end and a second end;
   a sleeve, having one end disposed within said second end of said body member and a terminal end extending therefrom;
   means for fixably mounting said one end of said sleeve within said second end of said body member;
   a piston, slidaby mounted relative to said body member and slidably received within said sleeve;
   urging means for urging said piston to a first position relative to said body member and said sleeve;
   means for moving said piston to a second position relative to said body member and said sleeve against said urging means;
   a first and a second electrode element;
   means for mounting at least one of said first and second electrode elements, for movement in accordance with the movement of said piston;
   means to control the divergence and convergence of said first and second electrode elements upon a reciprocating longitudinal movement of said piston;
   said first and second electrode elements disposed to grasp the living tissue when said piston is in said first position and disposed to release the living tissue when the piston is in said second position; and
   means for connecting said first and second electrode elements to the electrical power source to provide an electrical current flow relative to the living tissue; said connecting means including switch means mounted on said body member and means mounted on said piston cooperating with said switch means, to allow said electrical current flow only when said piston is in said first position.

2. A device as set forth in claim 1, wherein, said means for fixably mounting said sleeve within said second end of said body member includes an outwardly projecting annular flange at one end of said sleeve coacting with a guide and an aperture within said second end of said body member.

3. A device as set forth in claim 1, wherein, said piston includes a flange extending therefrom.

4. A device as set forth in claim 3, wherein, said urging means for urging said piston to a first position includes a spring mounted on said piston coacting with said flange on said piston and a guide within said body member.

5. A device as set forth in claim 1, wherein, said means for moving said piston to said second position relative to said body member and said sleeve includes a button extending from said first end of said body member.

6. A device as set forth in claim 5, wherein, said means for mounting at least one of said first and second electrode elements for movement in accordance with the movement of said piston includes said first and second electrode elements being integrally molded within said piston to extend along an internal region of said piston.

7. A device as set forth in claim 6, wherein, said first and second electrode elements extend from said second end of said body member into said sleeve, whereat, said first and second electrode elements are slidably received by said sleeve and further extend from said terminal end of said sleeve.

8. A device as set forth in claim 7, wherein, said means to control the divergence and convergence of said first and second electrode elements upon a reciprocating longitudinal movement of said piston includes, said terminal end of said sleeve, whereat, said first and second electrode elements withdraw to converge and grasp the living tissue upon said urging means urging said piston into said first position, and, extend to diverge and release the living tissue upon moving said piston into said second position against said urging means by the use of said button.

9. A device as set forth in claim 6, wherein, said means for connecting said first and second electrode elements to the electrical power source to provide an electrical current flow relative to the living tissue includes means mounted in said body member cooperating with means provided on said first and second electrode elements, the latter said means includes said first and second electrode elements terminating as contact arms extending perpendicularly to the axis of said piston and contact pads mounted within said body member, the cooperating said means being a circuit breaker, whereat, when said piston is in said first position contact is made between said contact arms and said contact pads, whereas, when said piston is in said second position said contact arms are displaced from said contact pads whereat there is no electrical continuity.

10. A device as set forth in claim 5, wherein, said means for mounting at least one of said first and second electrode elements for movement in accordance with the movement of said piston includes said first electrode element to be integrally molded within said piston to extend along an internal region of said piston.

11. A device as set forth in claim 10, wherein, said first electrode element extends from said second end of said body member into said sleeve, whereat, said first electrode element is slidably received by said sleeve and further extends from said terminal end of said sleeve, said device further including said second electrode element fixed to said body member and extending from said second end of said body member within said sleeve and further extending from said terminal end of said sleeve whereat said second electrode element is in a fixed position relative to said sleeve.

12. A device as set forth in claim 11, wherein, said means to control the divergence and convergence of said first and second electrode elements upon a reciprocating longitudinal movement of said piston, includes said terminal end of said sleeve whereat said first electrode element withdraws to converge toward said second electrode element to grasp the living tissue upon said urging means urging said piston into said first position, and, extends to diverge from said second electrode element and release the living tissue upon moving said piston into said second position against said urging means by the use of said button.

13. A device as set forth in claim 11, includes, said first electrode element which extends from said terminal end of said sleeve to be substantially hook-shaped, and, disposed to move longitudinally between said first and said second position enabling the tissue to be hooked by said first electrode element when said first electrode element is in said second position prior to engagement with the second electrode element; said second electrode element being in the shape of a projection.

14. A device as set forth in claim 10, wherein, said means for connecting said first and second electrode elements to the electrical power source to provide an electrical current flow relative to the living tissue includes, means mounted in said body member cooperating with means provided on said first electrode element, the latter said means includes said first electrode element terminating as a contact arm extending perpendicularly to the axis of said piston and a contact pad mounted within said body member, the cooperating said means being a circuit breaker, whereat, when said piston is in said first position contact is made between said contact arm and said contact pad, whereas, when said piston is in said second position said contact arm is displaced from said contact pad, whereat, there is no electrical continuity.

15. A device as set forth in claim 1, wherein, each of said first and second electrode elements includes an inwardly projecting tab.

16. A device as defined in claim 1, including means for connecting said electrode elements to a same polarity of said electrical power source to provide monopolar treatment of said living tissue.

17. A device as defined in claim 1, including means for connecting said electrode elements to different polarities of said electrical power source to provide bipolar treatment of said living tissue.

18. A device as set forth in claim 1, wherein, said switch means is manually operable for completing, when operated, a circuit between said power source and said electrode elements so that current flows only when said piston is in said first position and said switch means is operated.

19. A device as set forth in claim 18, wherein, said switch means includes first and second contact elements biased apart, an activator mounted in said body member positioned for engaging one of said contact elements to move that element toward the other contact element and, wherein, said cooperating means includes an elevated region on said piston positioned for engaging said other contact element when said piston is in said first position to move said other contact element toward said one element, so that, when said region engages said other contact element and said activator engages said one contact element, said contact elements are in electrical connection.

* * * * *